United States Patent [19]

Fink et al.

[11] Patent Number: 4,520,173

[45] Date of Patent: May 28, 1985

[54] MATERIAL FOR DEAERATING COATING SYSTEMS

[75] Inventors: Hans-Ferdi Fink; Otto Klocker; Koerner, Götz, all of Essen; Gert Künzel, Ratingen; Gerd Rossmy, Haltern-Lavesum; Christian Weitemeyer, Essen, all of Fed. Rep. of Germany

[73] Assignee: Th. Goldschmidt AG, Essen, Fed. Rep. of Germany

[21] Appl. No.: 482,947

[22] Filed: Apr. 7, 1983

[30] Foreign Application Priority Data

May 18, 1982 [DE] Fed. Rep. of Germany ....... 3218676

[51] Int. Cl.$^3$ ............................................. C08L 71/02
[52] U.S. Cl. .................................. 525/403; 524/267; 524/268; 524/269; 525/100; 525/101
[58] Field of Search ................. 525/403, 100, 101; 524/267, 268, 269

[56] References Cited

U.S. PATENT DOCUMENTS 3,203,919  8/1965  Brachman ........................... 524/269
3,699,067  10/1972  Stockman ........................... 524/269
3,945,957  3/1976  Noshiro et al. ..................... 524/269
4,278,774  7/1981  Nametkin et al. .................. 525/100

Primary Examiner—Melvyn I. Marquis
Attorney, Agent, or Firm—Toren, McGeady, Stanger, Goldberg & Kiel

[57] ABSTRACT

An aqueous composition for coating substrates which contains polymeric organic film formers containing a deaerating effective amount of a linear polymer having at least five side groups, each of which contains a silicon atom which is linked by way of a divalent hydrocarbon group to the polymer, each silicon atom carrying at least one $R^1$ group of formula $$O-[C_nH_{2n}O-]_xQ$$

in which n is 2 to 8, x is 1 to 10 and Q is an alkyl radical with 1 to 10 carbon atoms, an aryl radical, an alkaryl radical, or an acyl radical with 2 to 18 carbon atoms, and the sum of the carbon and oxygen atoms of $R^1$ is not less than 5, as well as the linear polymers themselves. Methods for preparation of such materials are also disclosed as well as their use.

6 Claims, No Drawings

MATERIAL FOR DEAERATING COATING SYSTEMS

BACKGROUND OF THE INVENTION

1. Field of the Invention

The invention relates to a material for deaerating coating systems which are applied from an aqueous phase onto surfaces and which contain polymeric organic film formers.

2. Description of the Prior Art

On applying water-dilutable coating systems onto a substrate and during or after the evaporation of the water from the aqueous dispersion, very small gas bubbles, finely dispersed in the coherent coating film being formed, frequently develop as the film is drying. These bubbles are sometimes referred to in the art as a microfoam. A portion of these bubbles float to the surface of the film where they burst and cause no defects, provided that the film is still sufficiently flowable for levelling the surface defects. Another portion of the bubbles rises to the surface. However, these bubbles do not burst. Rather, as the vehicle film cures, these bubbles form a very thin surface skin which can easily be damaged mechanically. Other bubbles remain dispersed in the film. Such defects in a paint film are described as "pin holes".

The phenomenon of this so-called microfoam is not to be compared with the behavior and appearance of a conventional, more or less finely dispersed, polyhedral foam. Known defoamers or antifoaming agents destroy the lamellae of such a foam, that is, the walls separating the individual foam bubbles, or prevent the formation of stable foam bubbles. In a microfoam, the individual, mostly spherical gas bubbles in water-dilutable coating systems are generally separated so far apart from each other, that no lamellae are formed between individual foam spheres. For this reason, known antifoaming agents generally fail to eliminate and remove the microfoam. The process of eliminating such microfoams is often referred to as deaerating. Further references to the differences in the behavior of spherical foam and polyhedral foam are given in "Ullmanns Encyclopädie der technischen Chemie" (Ullmann's Encyclopedia of Chemical Engineering), Vol. 20, pages 441 ff.

It is known that air bubbles, enclosed in hydraulic oils, lubricating oils or pickling fluids may be removed by additives. Such additives are described in German Auslegeschrift 23 05 257. These additives, however, fail to remove the microfoam from aqueous preparations.

It is presumed that processes at the gas/liquid interface affect the deaeration. The deaeration is possibly affected by changes in the viscosity of the coating system at the interface with the gas bubbles. In any case, because of the different physical and/or chemical influences on the interfaces between liquid and gas, those skilled in the art cannot draw conclusions from the effectiveness of antifoaming agents which might be applicable to the effectiveness of deaerating agents.

SUMMARY OF THE INVENTION

We have discovered a material and method for use thereof which is highly effective in deaerating microfoams in aqueous coating films. The bubbles of the microfoam become highly mobile and easily float to the surface, burst, and level out in a quantitative manner. The materials of the present invention are particularly suitable for deaerating coating systems which are applied from an aqueous phase to surfaces and contain organic film formers. Generally, such coating systems are aqueous preparations of film-forming organic substances, which optionally may contain soluble or insoluble pigments. The inventive materials are therefore intended especially for primers, paints, finishes and similar coating materials.

More particularly, we have discovered that such coating systems can be deaerated in a highly effective manner by addition of a composition which contains a linear polymer having at least five side groups, each of which contains a silicon atom which is linked by way of a divalent hydrocarbon group to the polymer, wherein each silicon atom carries at least one $R^1$ group having the formula $O-[C_nH_{2n}O-]_xQ$, in which $n=2$ to 8, $x=1$ to 10 and Q is an alkyl radical with 1 to 18 carbon atoms, an aryl radical, an alkaryl radical, or an acyl radical with 2 to 18 carbon atoms and wherein the sum of the carbon and oxygen atoms of $R^1$ are not less than 5.

The compositions are added to the coating system in quantities such that a deaerating effective amount of the polymer will be present in the coating system.

DESCRIPTION OF THE PREFERRED EMBODIMENTS

The polymers which are effective as deaerating agents, have a structure which may be described as having a comb structure. At least 5 groups are attached laterally to the linear back of the comb. The effectiveness of the compounds is presumably attributable to this structure of the polymeric molecule.

Thus, by suitably selecting and constructing the linear polymer carrying the side groups, that is, the back of the comb, those skilled in the art have at their disposal a method for matching the material to the structure of the substrate, which is to be deaerated.

The groups, linked laterally to the linear polymer, in each case have a silicon atom which is linked by way of a divalent hydrocarbon group to the linear polymer. The silicon atom of each side chain carries at least one $R^1$ group, which corresponds to the formula $O-[C_nH_{2n}O-]_xQ$. Q is an alkyl radical with 1 to 18 carbon atoms, an aryl radical, an alkaryl radical or an acyl radical with 2 to 18 carbon atoms. The sum of the oxygen and carbon atoms of the $O-[C_nH_{2n}O-]_xQ$ is not less than 5. Examples of Q radicals are the methyl, ethyl, propyl, isopropyl, butyl, isobutyl, decyl, dodecyl, oleyl, hexadecyl, phenyl, octylphenyl, nonylphenyl, dodecylphenyl, acetyl, or isobutyl radicals.

The subscript n has a value of 2 to 8, the subscript x a value of from 1 to 10.

Especially preferred examples of $R^1$ groups having the $O-[C_nH_{2n}O-]_xQ$ formula are the radicals $O-[C_3H_6O-]_4C_6H_5$; $-OC_2H_4OC_2H_5$; $-OC_4H_8OCH_3$;

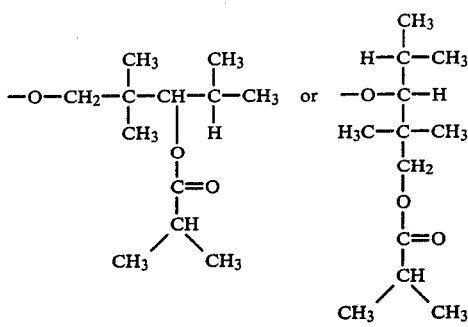

Especially preferred are materials which contain a linear polymer to which lateral structural units of the formula

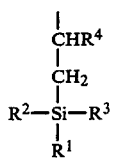

are linked. For these units, $R^1$ has the meaning given above. $R^2$ and $R^3$ may be the same or different and represent a $CH_3$— or $C_2H_5$-radical, a lower alkoxy radical with 1 to 6 carbon atoms or the $R^1$ radical. If $R^2$ and/or $R^3$ represents a lower alkoxy radical, attention must be paid to ensuring that the alkoxy radical does not hydrolyze in the aqueous coating system. If the coating systems have a neutral reaction in water, alkoxy radicals, with a low number of carbon atoms in the alkoxy radical, can be used without reservations. If, however, the coating system has an acidic reaction in the aqueous phase, the use of alkoxy radicals with 4 or more carbon atoms is recommended.

$R^4$ is a hydrogen or a methyl radical. Preferably, $R^4$ is a hydrogen radical.

In much the same way as the structure of the linear polymer can be adapted to the structure of the organic film former, it is advisable to adapt the lateral groups, and especially the O—$[C_nH_{2n}O$—$]_xQ$ group to the coating system, and moreover, especially to the solvent, which ensures the film formation of the organic film former. If, for example, phenyl glycol is used as solvent, it is advisable to use a structure such as —O—$[C_3H_6O$—$]_4C_6H_5$ as the O—$[C_nH_{2n}O$—$]_xQ$ group. If methoxybutanol is used as the film-forming solvent, the methoxybutoxy group proves to be particularly suitable as the $R^1$ group.

Especially preferred polymers, which are contained as active substances in the deaerating agents, can be characterized by the following formulas.

For example, a polymer of formula

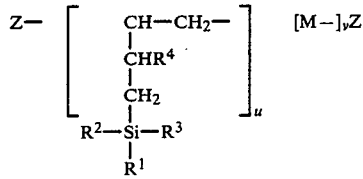

is particularly suitable for deaerating coating systems, which are based on acrylate resins. In the formula, $R^1$, $R^2$, $R^3$ and $R^4$ have the meanings already given. Z are terminal groups which hardly have any influence on the effectiveness of the polymers and are determined by the nature of the polymerization process. Examples of such groups are the hydrogen, $C_1$ to $C_5$ alkyl or alkenyl, or the phenyl radical. The two Z groups may be the same or different.

The structure units which are important for the purpose of the present invention, are those which have the subscript u. In accordance with the definition, u is not less than 5.

The linear polymer can additionally have chain forming M units. These M units are specified by the value of v, v being given by the quotient $u/v \geq 4$. The quotient $u/v$ preferably has a value of not less than 8. This means that preferred linear polymers are those in which the structure units described by the subscript u, are contained in predominant numbers.

In the case of a copolymerization, the different units are distributed statistically, corresponding to their reactivities. Examples of M units are

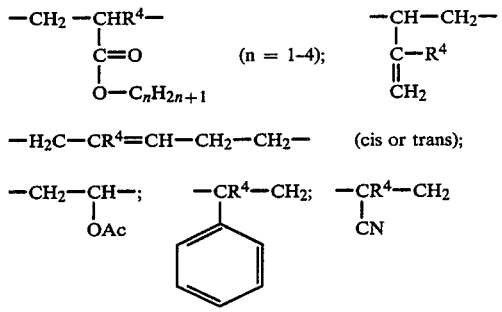

Compounds of the aforementioned formula can be synthesized by known procedures by first of all synthesizing copolymers having the formula

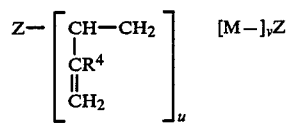

Such polymers can be synthesized by known procedures by polymerizing, for example, 1,3-butadiene with organometallic catalysts which contain metals, such as, for example, Li, Na, Co, Mo, Ti, V or Al individually, or in admixture. Suitable processes are described, for example, in German Offenlegungsschrift No. 29 33 609 and in Markromol, Chem. 16, page 213, 1955.

Hydrogenchlorosilanes, for example, $CH_3HSiCl_2$ or $HSiCl_3$ or $(CH_3)_2HSiCl$, are then added to the copolymers by a hydrosilation reaction. At the end, the chlorine can be esterified with the HO$[C_nH_{2n}O]_xQ$ compounds by themselves or in admixture with low molecular weight alcohols having 1 to 6 carbon atoms, the inventive substances which are suitable as deaerators, then being formed. Especially suitable are products based on polybutadiene with a high content of vinyl groups, that is,

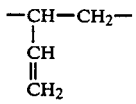

groups.

Other linear polymers, which are also very suitable, can be represented by the formula

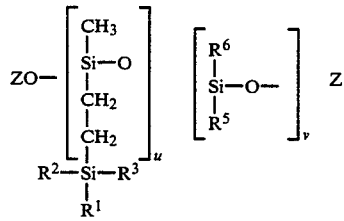

The substituents $R^1$, $R^2$ and $R^3$ and the subscripts u and v have the already-given meaning or the aforementioned values. The $R^5$ and $R^6$ substituents are alkyl radicals, such as, for example, methyl, ethyl, hexyl or octadecyl radicals. They may be phenyl radicals or also represent the hydrogen radical. In this case, however, not more than 10 mole percent of all silicon atoms contained in the polymeric molecule, can have a hydrogen radical and $R^5$ and $R^6$ cannot both be hydrogen. $R^5$ and $R^6$ methyl radicals are preferred. The Z radicals once again are terminal groups and, generally, are trimethylsilyl radicals. The aforementioned compounds can be synthesized by known procedures by synthesizing siloxanes having the formula:

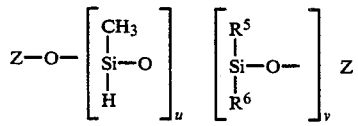

by equilibrating suitable building blocks. In the preceding formula, Z preferably is $(CH_3)_3Si-$ and $R^5$ and $R^6$ preferably are $CH_3$. Vinyl silanes, for example

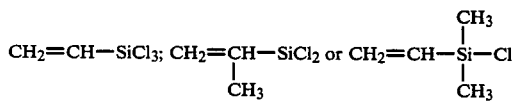

are then added to this siloxane in a hydrosilylating reaction.

Finally, the Si-Cl groups are esterified, as already explained just above, in order to obtain the products, which are to be used according to the invention.

Like polymeric organosilicon compounds in general, these compounds lower the interfacial tension in a special manner. They are suitable for deaerating organocarbon as well as organosilicon coating systems.

A further group of effective compounds is represented by the formula

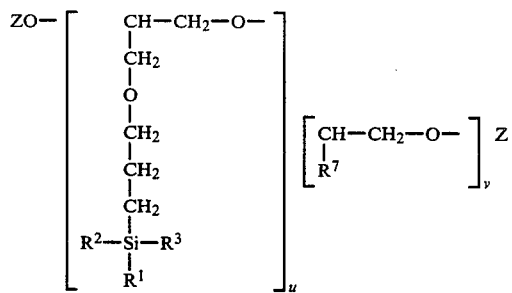

The substituents $R^1$, $R^2$ and $R^3$ and the subscripts u and v have the meaning or value already given. $R^7$ is a hydrogen radical or an alkyl radical with 1 to 18 carbon atoms, preferably, the methyl radical. $R^7$ can also represent the $-CH_2OCH_2CH=CH_2$ or the $-CH_2OR^8$, $R^8$ being an alkyl radical with 1 to 18 carbon atoms or a phenyl radical. Z once again represents terminal groups, preferably, lower alkyl groups with 1 to 4 carbon atoms, or trimethylsilyl groups. The compounds can be synthesized by known methods from the corresponding alkylene oxides. Usually alkylene oxides of the formula

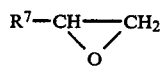

are copolymerized with allyl glycidyl ether, using acidic or alkaline catalysts. Products of the following formula are formed

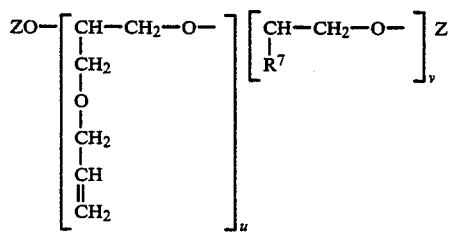

The Z group results from the starting molecule used, it is H, when a glycol of the formula below is used as the starter.

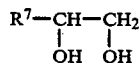

If a monofunctional alcohol, for example, $C_4H_9OH$, is used as starter, Z consists to the extent of 50 mole percent of $C_4H_9$ units and to the extent of 50 mole percent of H. OH groups in the molecule are generally blocked by esterification or etherification, for example, they can be trimethylsilylated, before the reaction with hydrogen silanes is carried out. The polyethers, containing allyl side groups, are hydrosilylated with hydrogenchlorosilanes, for example, $CH_3HSiCl_2$, $(CH_3)_2HSiCl$ or $HSiCl_3$. Finally, the SiCl groups are esterified, in order to arrive at the compounds which are to be used inventively.

The inventive materials usually contain the aforementioned active substances as a solution in organic solvents. It is possible to produce preparations of relatively high concentration. For example, the inventive materials for deaerating may contain polymers, which have linear side chains, in amounts of 5 to 60 weight percent. The inventive materials may contain additional additives, which favor the deaerating effect. For instance, it has proven to be particularly advantageous to add to the inventive materials, hydrophobized, finely divided silica in amounts of 2 to 30 weight percent, based on the preparation. The finely divided silica should have a BET surface area of at least 50 m$^2$/g. The finely divided silica is hydrophobized, advisably by siliconizing it, employing known procedures.

The inventive materials are added to the water-dilutable coating systems in amounts of 0.05 to 1 weight percent, based on the vehicle. It is obvious to those skilled in the art that the solvent used, in which the linear polymers are dissolved, must be compatible with the solvents in which the coating systems are contained.

The usual paint properties, such as, hardness, gloss and adhesion to the substrate, are not impaired by the inventive deaerating agents.

The synthesis of the active substances contained in the inventive materials, the preparation of the inventive deaerating agents and the use of these agents are shown in the following examples.

EXAMPLE 1

To a reactor, equipped with stirrer, reflux condenser, thermometer and dropping funnel, are added 2,000 g of 1,2-polybutadiene dissolved in 6,400 g of toluene and having an equivalent weight of 60.14 g based on the vinyl group content and corresponding to the average formula:

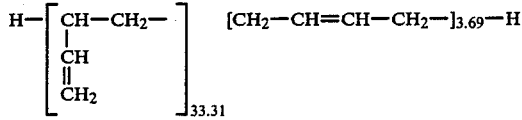

This solution is heated with stirring to 60° C., mixed at this temperature with 500 mg of hexachloroplatinic acid dissolved in 4 ml of tetrahydrofuran (catalyst solution) and heated to 75° C. Then, 4,208 g of methylhydrogen dichlorosilane (that is, 110% of the amount required for addition to the vinyl groups) are allowed to run in slowly. The rate of addition is controlled so that the temperature of the contents of the flask does not exceed 100° C. After completing the addition of the silane, the reactants are kept for 1 hour at 100° C., in order to complete the reaction. Subsequently, the excess methylhydrogen dichlorosilane and a part of the toluene are distilled off. The distillation is ended when the temperature of the vapors coming over reaches 110° C. The remaining contents of the flask are cooled down and the solids content and the content of hydrolyzable chlorine, expressed as milliequivalents per g of solids, are determined on the toluene solution of the reaction material.

The solution of the reaction product has a solids content of 44.1% and an acid value of 11.15 milliequivalents/g based on the solvent-free product. From these values, the equivalent weight of the solid is calculated to be 89.69 g.

In order to synthesize compounds having the formula

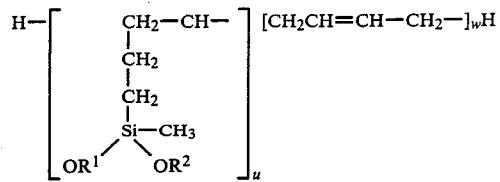

wherein
u=33.31
w=3.69
u:w=9.027, for use in the present invention, 89.69 g of solids, corresponding to 203.37 g of the 44.1% solution of the abovedescribed methylhydrogen dichlorosilane adduct on 1,2-polybutadiene are added in each case to a reactor equipped with stirrer, thermometer, reflux condenser and dropping funnel. A 20 weight percent solution of the ROH in toluene is allowed to flow in at 70° C. within 1 hour. After the addition is completed, the reaction is allowed to continue for a further hour at 70° C. The product is then cooled to about 40° C. and the hydrogen chloride present in the reaction material is neutralized by the dropwise addition of triethylamine to the point of alkaline reaction. After the reaction product is cooled to room temperature, the precipitated triethylammonium hydrochloride is filtered off and the toluene is removed from the filtrate by distillation. The inventive substances remain in the residue. A number of polymers, synthesized by this process, are listed in the following table.

TABLE 1

| Compound | $O-[C_2H_{2n}O]_x Q =$ |
|---|---|
| 1a | $-O-[C_3H_6O]_4-C_6H_5$ |
| 1b | $-O-[C_2H_4O]_1-C_6H_5$ |
| 1c | $-O-C_8H_{16}O-\overset{O}{\underset{\|}{C}}-C_3H_7\ -CH_2-\underset{\underset{CH_3}{\|}}{\overset{C_8H_{16}=CH_3}{\underset{\|}{C}}}-CH-\underset{\underset{CH_3}{\|}}{\overset{CH_3}{CH}}$ |
| 1d | $-OC_2H_4OC_2H_5$ |
| 1e | $-O-C_4H_8OCH_3$ |

Polymers 1a to 1e, which are listed in Table 1, are incorporated in a concentration of 0.1 weight percent in a white paint, which is prepared from a poly(ethyl acrylate) dispersion and has a pigment volume concentration of about 18% and a solids content of 48%. In order to make the incorporation of the inventive compounds easier, 40 weight percent solutions of compounds 1a to 1e in a mixture of equal parts of ethylene glycol and solvent naphtha are prepared first and these solutions are incorporated into the plant with the help of a dissolver. 24 hours after mixing, 100 g of the paint are stirred in a 250 ml beaker for 1 minute with a turbine stirrer at 2,000 rpm and the paint is then applied with a 200 μm spiral blade on a clean, grease-free glass plate. After the plates have been allowed to dry in a dust-free room, they are illuminated from below with a strong light source and the number of very fine holes, described as "pinholes", is counted in a 100 cm$^2$ area. Advisably, the film is examined with a magnifying glass.

The result is summarized in Table 2. The numbers are the average values of three independently applied paint films.

TABLE 2

| Compound | Number of Pinholes per 100 cm² |
|---|---|
| 1a | 4 |
| 1b | 7 |
| 1c | 12 |
| 1d | 4 |
| 1e | 10 |
| without additive | several hundred |

EXAMPLE 2

Before being dissolved in the mixture of equal parts of ethylene glycol and solvent naphtha, the compounds described in Example 1 are mixed with a conventional, commercial, hydrophobized silica, which has a specific surface area of 150 m² and a primary particle size of approx. 15 nm. The mixture consists of 85 parts by weight of the compounds 1a to 1e and 15 parts by weight of the hydrophobic silica. These mixtures are dissolved as described in Example 1 and added to the white paint. Testing is carried out by the method described in Example 1. The results are summarized in Table 3.

TABLE 3

| Hydrophobic Silica-Containing Preparations of Compound | Number of Pinholes per 100 cm² |
|---|---|
| 1a | 0 |
| 1b | 2 |
| 1c | 4 |
| 1d | 0 |
| 1e | 0 |
| without additive | several hundred |

EXAMPLE 3

In a reactor, equipped with stirrer, thermometer, reflux condenser and dropping funnel, 200 parts by weight of a poly(allyl glycidyl ether) having the formula

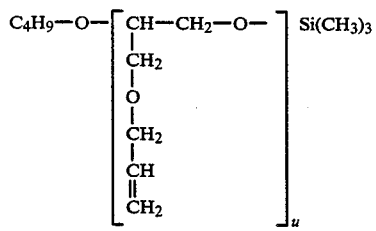

wherein u=28.20
are dissolved in 400 parts by weight of toluene and heated with stirring to 60° C. A solution of 400 mg of hexachloroplatinic acid in 4 ml of tetrahydrofuran is then added, followed by 212.0 g of methyldichlorosilane (that is, 110% of the amount required for addition to the allyl group), which is added dropwise. At the same time, the contents of the flask are heated to 100° C. Upon completing the addition of the silane, the reaction mixture is held for 1 hour at 100° C. in order to complete the reaction. The excess methylhydrogendichlorosilane and a portion of the toluene are then distilled off. The distillation is stopped when the vapors coming over have reached a temperature of 110° C. The adduct, dissolved in toluene and remaining in the reactor, has a solids content of 52.2 weight percent and an acid value of 8.48 milliequivalents/g. From this, the conversion of allyl groups is calculated to be 99.4%. From this value, the average formula is calculated to be

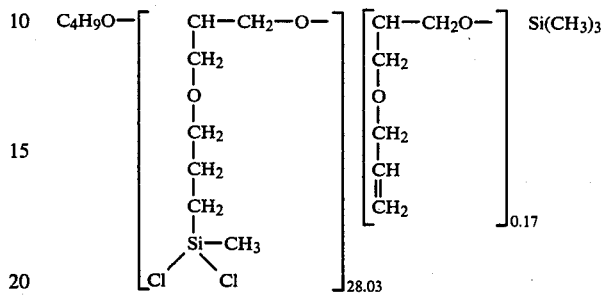

wherein
u=28.03
w=0.17
u/w=164.88

In order to synthesize inventive compounds of formula

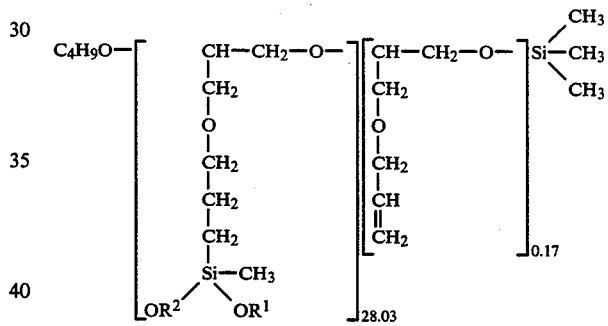

117.9 parts by weight of the methylhydrogendichlorosilane adduct, prepared in the manner described above, or 226.9 parts by weight of the 52.2 weight percent solution in toluene, are added to a reactor which is equipped with stirrer, thermometer, reflux condenser and dropping funnel, and heated to 70° C. A solution of 359.0 parts by weight of $C_6H_5-[OC_3H_6-]_4OH$ in 500 g of toluene, corresponding to 110% of the theoretically required amount, is then added dropwise. At the end of the addition, the reaction is allowed to continue for 1 hour at 70° C. The reaction mixture is then cooled to 40° C. and the hydrogen chloride remaining in the mixture, is neutralized by the dropwise addition of triethylamine until an alkaline reaction is obtained. The mixture is then cooled to room temperature, the precipitated triethylammonium chloride is filtered off the the filtrate is freed from toluene by distillation.

The residue is tested in the manner described in Example 1. No pinholes can be detected in 100 cm² of paint film.

EXAMPLE 4

A reactor, equipped with stirrer, thermometer, reflux condenser and dropping funnel, is charged with 1,000 g of an α,ω-trimethylsilylpolymethylhydrogen siloxane having the formula

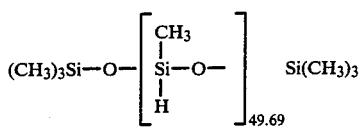

dissolved in 2,250 g of toluene and the temperature is raised to 90° C. Then 200 mg of hexachloroplatinic acid, which is dissolved in 4 ml of tetrahydrofuran, is added and 2,448 g of methylvinyl dichlorosilane (that is, 110% of the amount required for addition to the SiH groups) is allowed to run in during 1 hour. While the silane is being added, the temperature rises to 108° C. When all the silane has run in, the reaction is allowed to continued for 1 hour at the refluxing temperature. The excess methylvinyl dichlorosilane and a portion of the toluene are then distilled off, until a total of about 1,700 g of distillate has been removed. The adduct, dissolved in the toluene and remaining in the reactor, has a solids content of 80.9 weight percent and an acid value of 9.77 milliequivalents/g, based on the solvent-free product. This corresponds to practically a complete addition of the SiH used to the methyldichlorosilane. The compound formed can accordingly be assigned the following average formula:

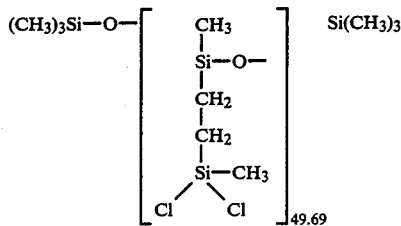

From the acid value, an equivalent weight of 102.35 g can be calculated for the solid.

In order to prepare inventive compounds of the general formula

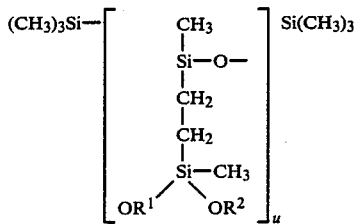

156.4 parts by weight of the 80.9% toluene solution of the above-described adduct, corresponding to one SiCl equivalent, are reacted in each case with compounds having OH groups in the manner described in Example 1.

A series of polymers, synthesized by this process, are listed in Table 4.

TABLE 4

| Compound | OR$^1$=OR$^2$ |
|---|---|
| 4a | —O[C$_3$H$_6$O]$_4$C$_6$H$_5$ |
| 4b | —OC$_2$H$_4$—OC$_2$H$_5$ |
| 4c | —O—C$_4$H$_8$—OCH$_3$ |

The polymers 4a–4c, listed in Table 4, are tested for their deaerating effect by the procedure described in Example 1.

The results are given in Table 5.

TABLE 5

| Compound | Number of Pinholes per 100 cm$^2$ |
|---|---|
| 4a | 2 |
| 4b | 6 |
| 4c | 4 |
| without additive | several hundred |

COMPARISON EXAMPLE (similar to DE-AS 23 05 257)

The following compounds are introduced at a level of 0.1 weight percent and in the form of a 40% solution in a mixture of equal parts of ethylene glycol and solvent naphtha into the white paint described in Example 1.

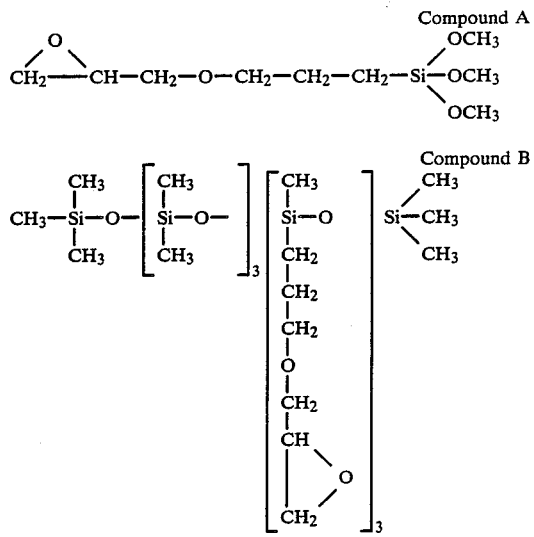

The paints were tested in the manner described in Example 1 and compared with an additive-free paint film. The number of pinholes per 100 cm$^2$ is approximately the same in all three samples. A deaerating effect cannot be detected.

We claim:

1. In an aqueous phase coating composition which contains polymeric, organic film formers, the improvement which comprises said composition containing a deaerating effective amount of a linear polymer having at least five side groups, each of which contains a silicon atom which is linked by way of a divalent hydrocarbon group to the polymer, each silicon atom carrying at least one R$^1$ group of formula O—[C$_n$H$_{2n}$O—]$_x$Q in which
n is 2 to 8,
x is 1 to 10 and
Q is an alkyl radical with 1 to 10 carbon atoms, an aryl radical, an alkaryl radical, or an acyl radical with 2 to 18 carbon atoms,
and the sum of the carbon and oxygen atoms of R$^1$ is not less than 5.

2. The composition of claim 1 wherein the linear polymer has lateral structural units linked to it having the formula

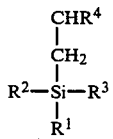

in which
R² and R³ are the same or different and represent a CH₃— or C₂H₅-radical, a lower alkoxy radical with 1 to 6 carbon atoms or the R¹ radical, and
R⁴ is a hydrogen or methyl radical.

3. The composition of claim 2 wherein the linear polymer has the formula

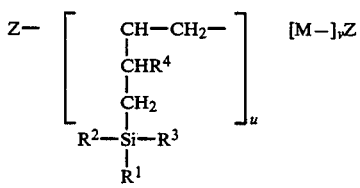

in which
M is a chain-forming monomer unit,
Z is a terminating group,
u is not less than 5, and the quotient u/v is not less than 0.4.

4. The composition of claim 1, 2, or 3, which further contains hydrophobic, finely divided silica, having a BET surface area of at least 50 m²/g in amounts of 30 weight percent, based on the weight of the composition.

5. The composition of claim 2 wherein the linear polymer has the formula

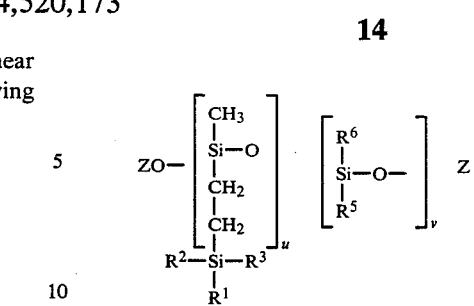

wherein R⁵ and R⁶ are the same or different and represent an alkyl, phenyl or hydrogen radical, in which not more than 10 mole percent of all silicon atoms may contain an SiH group and R⁵ and R⁶ cannot at the same time represent a hydrogen radcal; Z is a terminating group; u is not less than 5; and the quotient u/v is not less than 0.4.

6. The composition of claim 1 wherein the linear polymer has the formula

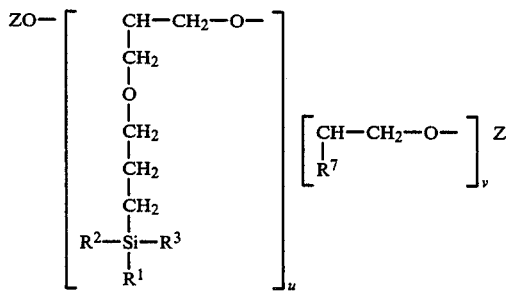

wherein
R⁷ is a hydrogen or alkyl radical with 1 to 18 carbon atoms or the —CH₂OCH₂CH=CH₂ or —CH₂OR⁸ group and R⁸ is an alkyl radical with 1 to 18 carbon atoms or a phenyl radical;
u is not less than 5; and the quotient u/v is not less than 0.4.

* * * * *